United States Patent [19]

Taylor

[11] 4,332,252

[45] Jun. 1, 1982

[54] DRAINAGE RECEPTACLE WITH SUPPORT MEMBER

[75] Inventor: Rebecca S. Taylor, Palatine, Ill.

[73] Assignee: The Kendall Company, Boston, Mass.

[21] Appl. No.: 167,492

[22] Filed: Jul. 11, 1980

[51] Int. Cl.$^3$ .......................... A61F 5/44

[52] U.S. Cl. .......................... 128/275; 128/DIG. 24; 248/95; 248/328

[58] Field of Search .......................... 128/275, DIG. 24; 224/254; 248/95, 328; 24/186, 115 G, 115 K, 268, 30.5 S

[56] References Cited

U.S. PATENT DOCUMENTS 3,568,965 3/1971 Clark .......................... 248/95

FOREIGN PATENT DOCUMENTS 384453 2/1965 Switzerland .......................... 24/30.5 S 2028413 3/1980 United Kingdom .......................... 24/30.5 S

*Primary Examiner*—Kyle L. Howell

*Assistant Examiner*—J. L. Kruter

*Attorney, Agent, or Firm*—Powell L. Sprunger

[57] ABSTRACT

A drainage receptacle comprising, a container having a chamber for receiving body fluids and a pair of spaced apertures adjacent an upper portion of the container. The receptacle has a support member having a pair of spaced openings and a hook. The receptacle also has an elongated cord passing through the apertures with an end portion extending from each of the apertures and a central portion extending between the apertures. The end portions of the cord are received in the openings of the support member and the cord central portion is received on the hook.

8 Claims, 4 Drawing Figures

Fig. 1
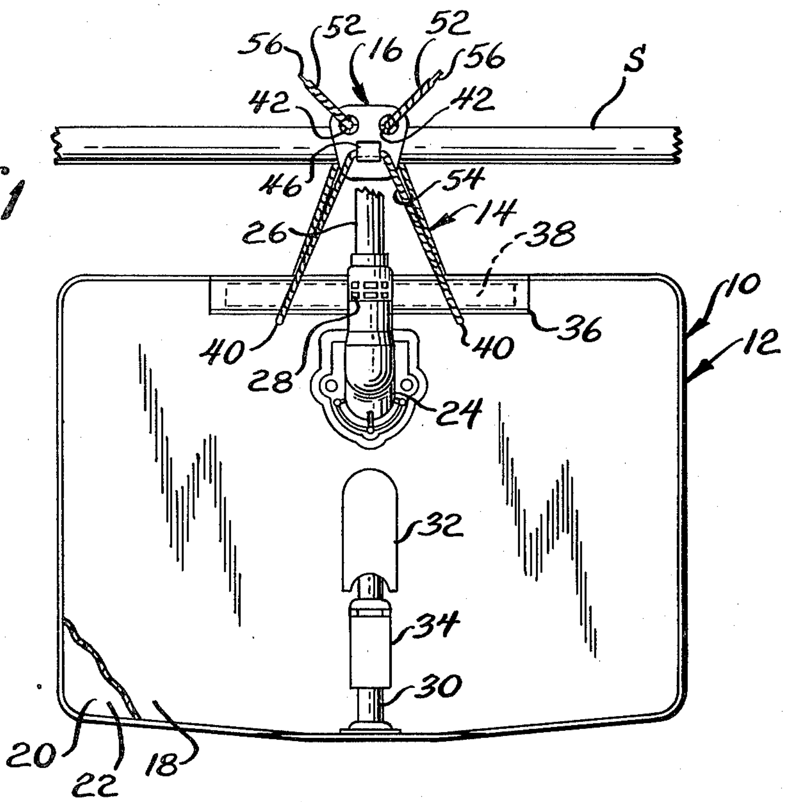
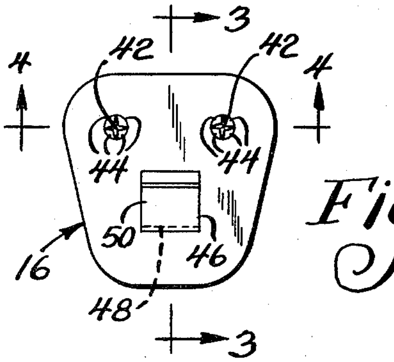
Fig. 2
Fig. 3
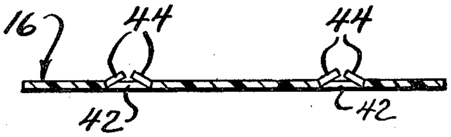
Fig. 4

DRAINAGE RECEPTACLE WITH SUPPORT MEMBER

BACKGROUND OF THE INVENTION

The present invention relates to drainage receptacles for urine.

Before the present invention, a number of collection bags have been proposed for collecting urine. Such bags have a drainage tube with a downstream end communicating through a connector with a chamber in the bag. In use, a catheter is placed in a patient, and an upstream end of the drainage tube is attached to a proximal end of the catheter outside the patient, such that urine drains from the bladder through the catheter and drainage tube to the bag chamber for collection therein. Although such drainage bags serve for the intended purpose of collecting urine from the patient, many times it is desirable to attach the bag to a support structure, such as a bed rail. Accordingly, it is desirable to facilitate the attachment procedure of the bag in order to minimize the inconvenience and required time of hospital personnel for this purpose.

SUMMARY OF THE INVENTION

A principal feature of the present invention is the provision of an improved drainage receptacle for collecting urine.

The receptacle of the invention comprises, a container having a chamber for receiving body fluids and a pair of spaced apertures adjacent an upper portion of the container. The receptacle has a support member having a pair of spaced openings and a hook. The receptacle also has an elongated cord passing through the apertures with an end portion extending from each of the apertures and a central portion extending between the apertures.

A feature of the present invention is that the end portions of the cord are passed through the openings of the support member and the cord central portion is received on the hook of the support member in order to support the container on a support structure by the support member and cord.

Another feature of the invention is that the cord may be connected to the support member in a simplified manner in order to facilitate attachment of the container to the support structure.

Still another feature of the invention is that the end portions of the cord may be adjusted in the openings of the support member in order to modify the height of the container below the support structure.

Further features will become more fully apparent in the following description of the embodiments of this invention and from the appended claims.

DESCRIPTION OF THE DRAWINGS

In the drawings:

FIG. 1 is a front plan view, partly broken away, of a drainage receptacle of the present invention;

FIG. 2 is a front plan view of a support member for the drainage receptacle of FIG. 1;

FIG. 3 is a sectional view taken substantially as indicated along the line 3—3 of FIG. 2; and FIG. 4 is a sectional view taken substantially as indicated along the line 4—4 of FIG. 2.

DESCRIPTION OF THE PREFERRED EMBODIMENTS

Referring now to FIG. 1, there is shown a drainage receptacle generally designated 10 comprising a container 12, an elongated cord 14, and a support member 16. The container 12 has a front wall 18 of flexible plastic material, and a back wall 20 of flexible plastic material, with the walls 18 and 20 being joined at their periphery by suitable means, such as heat sealing, in order to define a chamber 22 between the front and back walls 18 and 20. The container 12 has a hollow connector 24 comprising a drip chamber attached to an upper portion of the front wall 18 with the connector 24 communicating with the chamber 22. The receptacle 10 has a drainage tube 26 with a downstream end received in the connector 24 such that a lumen in the drainage tube 26 communicates with the connector 24. As shown, the connector 24 may have a suitable vent 28 comprising openings in the connector 24 and a bacteria filter of known type to filter bacteria from the air passing from the atmosphere into the connector 24 and chamber 22.

The container 12 has a tubular section 30 attached to a lower portion of the front wall 18 with the tubular section 30 communicating with the chamber 22. The container 12 has a pocket 32 on the front wall 18 to receive an outer end of the tubular section 30 in a storage position of the tubular section 30. The tubular section 30 has a clamp 34 of suitable type in order to releasably close the tubular section 30. In use, the tubular section 30 is removed from the pocket 32 and the clamp 34 is released in order to drain urine from the container chamber 22, after which the clamp 34 is again closed and the outer end of the tubular section 30 is inserted into the pocket 32 in order to retain the tubular section 30 in its storage position. The container 12 has an elongated sleeve 36 with open ends to receive a relatively rigid support bar 38 in the sleeve 36. As shown, the container 12 has a pair of spaced apertures 40 in an upper portion of the container 12 below the sleeve 36 on opposed sides of the connector 24.

The support member 16 comprises a thin plate of flexible plastic material. With reference to FIGS. 1–4, the support member 16 has a pair of laterally spaced openings 42 adjacent an upper portion of the support member 16. The openings 42 may be formed by punching the plate along perpendicular lines in order to form a plurality of bosses 44 extending around the openings 42 for a purpose which will be described below. The support member 16 also has a lower hook 46 which may be punched from the plate, with the hook 46 having a first flange 48 extending outwardly from the plate, and a second flange 50 extending upwardly from an outer end of the first flange 48.

The cord 14 is passed through the spaced apertures 40 of the container 12 with opposed end portions 52 of the cord 14 extending from the apertures 40 on the rear side of the container 12, and with a central portion 54 of the cord 14 extending between the pair of apertures 40 on the front side of the container 12. The cord 14 may have plastic covered opposed ends 56 of reduced dimensions for a purpose which will be described below.

In use, the cord 14 is passed through the apertures 40 of the container 12 in the described configuration with the end portions 52 of the cord 14 extending from apertures 40, and with the central portion 54 of the cord 14 located on the front of the container 12. Next, the end portions 52 of the cord 14 are threaded through the spaced openings 42 of the support member 16, with the covered ends 56 of the cord 14 facilitating passage of the end portions 52 through the support member openings 42. After placement of the end portions 52 of the cord 14 in the support member openings 42, the bosses 44 of the support member 16 frictionally engage the cord in order to retain the cord end portions 52 in place. Next, the support member 16 with attached cord end portions 52 is placed over the rear of a supporting structure S, such as a bed rail, and the central portion 54 of the cord 14 is lifted to the support member 16 and attached to the hook 46 of the support member 16. In this configuration, the support member 16 and cord 14 support the container 12 from the supporting structure S. The height of the container 12 relative to the support structure S may be modified by changing the length of the cord end portions 52 which extend through the openings 42 of the support member 16. The container 12 may be readily removed from the support structure S by removing the central portion 54 of the cord 14 from the support member hook 46.

Thus, in accordance with the present invention the container 12 may be readily attached to and removed from a supporting structure S in order to selectively support the container 12 at a location above the floor. Also, the height of the container 12 relative to the support structure S may be readily modified by adjusting the position of the cord end portions 52 in the openings 42 of the support member 16.

The foregoing detailed description is given for clearness of understanding only, and no unnecessary limitations should be understood therefrom, as modifications will be obvious to those skilled in the art.

I claim:

1. A drainage receptacle, comprising:

a container having a chamber for receiving body fluids and a pair of spaced apertures adjacent an upper portion of the container;

a support member having a pair of spaced openings and a hook; and an elongated cord passing through said apertures with an end portion extending from each of the apertures and a central portion extending between said apertures, said end portions of the cord being received in said openings of the support member and said cord central portion being received on said hook, said support member having means for frictionally engaging and slidably receiving said end portions of the cord in said openings such that said end portions may be adjusted in said openings and such that the height of the receptacle may be adjusted during the time the receptacle is being filled.

2. The receptacle of claim 1 wherein said support member engaging means comprises a plurality of bosses surrounding said openings to grip said cord end portions.

3. The receptacle of claim 1 wherein said openings are located adjacent an upper portion of the support member and said hook is located adjacent a lower portion of the support member.

4. The receptacle of claim 1 wherein said support member comprises a plastic plate.

5. The receptacle of claim 4 wherein said hook comprises a portion removed from said plate.

6. The receptacle of claim 4 wherein said hook comprises a first outwardly directed flange, and a second flange extending upwardly from an outer end of the first flange.

7. The receptacle of claim 1 wherein the container includes a central connector communicating with said chamber, and in which said apertures are located on opposed sides of the connector.

8. The receptacle of claim 1 wherein said container has a pair of opposed flexible walls defining said chamber.

* * * * *